United States Patent [19]
Zwingenberger et al.

[11] Patent Number: 5,545,383
[45] Date of Patent: Aug. 13, 1996

[54] PRESSURE HOUSING FOR A STERILIZATION CHAMBER FOR STEAM STERILIZATION OF MEDICAL INSTRUMENTS, IMPLANTS AND THE LIKE

[75] Inventors: Arthur Zwingenberger, Toronto, Canada; Martin Saupe, Offenbach, Germany

[73] Assignee: Sci-Can, Toronto, Canada

[21] Appl. No.: 371,532

[22] Filed: Jan. 10, 1995

[30] Foreign Application Priority Data

Jan. 18, 1994 [EP] European Pat. Off. ............. 94100657

[51] Int. Cl.⁶ ................................................ A61L 2/06
[52] U.S. Cl. ............................................ 422/295; 422/292
[58] Field of Search ................. 422/26, 292, 295, 422/297, 300; 220/4.01, 4.28, 401, 23.86, 410, 668; 312/258.1, 263, 264

[56] References Cited

U.S. PATENT DOCUMENTS

| | | | |
|---|---|---|---|
| 3,105,617 | 10/1963 | Felldin | 220/668 |
| 4,824,644 | 4/1989 | Cox | 422/300 |
| 5,083,673 | 1/1992 | Fossey | 220/401 |
| 5,271,893 | 12/1993 | Newman | 422/26 |
| 5,290,511 | 3/1994 | Newman | 422/26 |

FOREIGN PATENT DOCUMENTS 2597185  10/1987  France.

Primary Examiner—Robert J. Warden
Assistant Examiner—Theresa T. Snider
Attorney, Agent, or Firm—McAulay Fisher Nissen Goldberg & Kiel, LLP

[57] ABSTRACT

A pressure housing for a sterilization chamber for steam sterilization of medical instruments, implants and the like, having upper, lower and side walls in the form of individual thermally insulating plates which are arranged in central openings of at least two identically constructed frame parts held in positive engagement in a carrier and are held so as to contact the inner edges of the openings in a positive engagement.

7 Claims, 4 Drawing Sheets

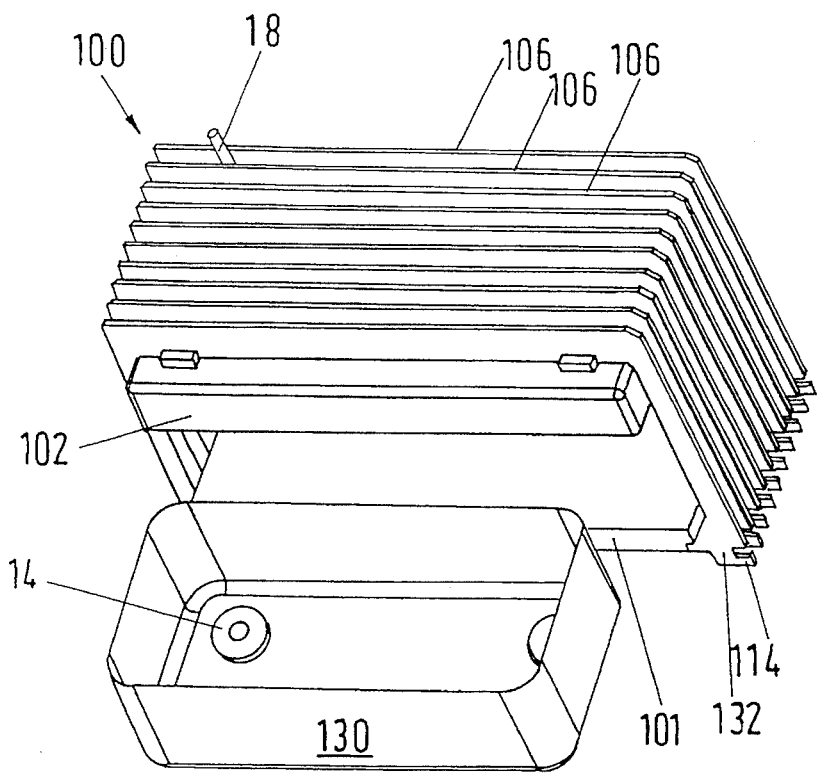
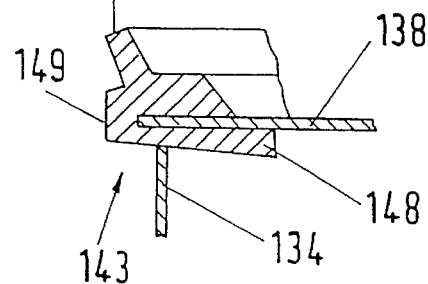
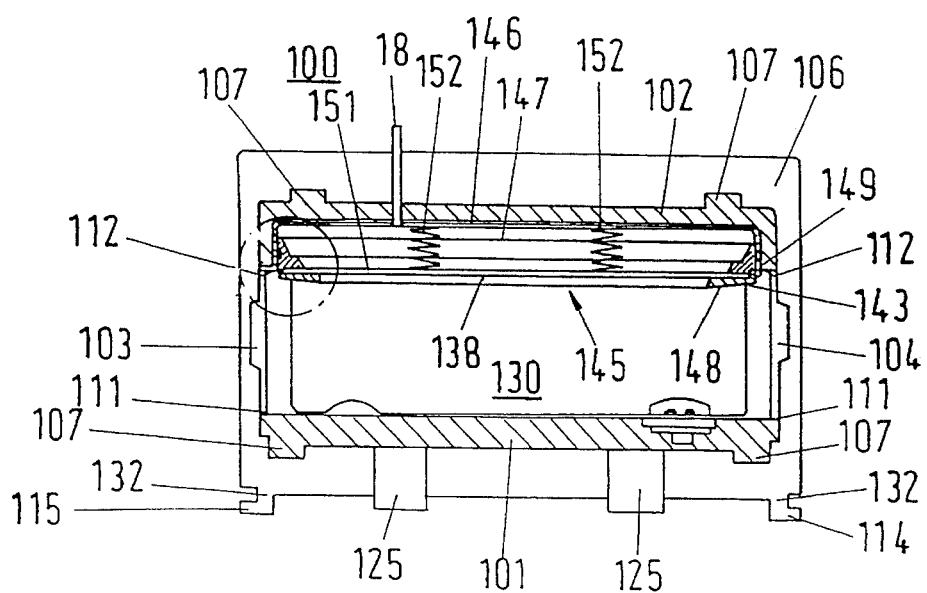

5,545,383

PRESSURE HOUSING FOR A STERILIZATION CHAMBER FOR STEAM STERILIZATION OF MEDICAL INSTRUMENTS, IMPLANTS AND THE LIKE

BACKGROUND OF THE INVENTION

1. Field of the Invention

The invention is directed to a pressure housing for a sterilization chamber receiving a sterilization vessel.

2. Description of the Related Art

In order to curb costs in medicine and to prevent waste requiring special disposal, it is necessary to abandon the use of disposable instruments, as they are called, and return to instruments which may be used repeatedly, which calls for the reinstitution of sterilization techniques. To this end, costly autoclaves have been replaced by energy-saving small devices which can be used for fast and economical sterilization of instruments at the location of their use (see EP 0429 960).

In the known arrangement, the sterilization vessel is constructed as a detachable cassette whose base part and cover part are held so as to be pressed together tightly in a holding device during the sterilizing process by flange-like edges with the intermediary of a seal.

However, the construction of the sterilization vessel as a cassette formed by two parts and closed on all sides toward the outside atmosphere has proven costly to manufacture. Further, close tolerances must be maintained during production to enable coupling with the associated feed lines and outlet lines when the cassette is slid into the holding device.

Therefore, there exists a need for further simplification of such devices, particularly with respect to the construction of the necessary pressure housing receiving the sterilization vessel and with respect to loading the pressure housing with instruments to be sterilized while at the same time reducing manufacturing costs.

However, the relatively close tolerances for the pressure-tight closing of the sterilization space which is indispensable to its operation and must be ensured over a long period of use in spite of sharply fluctuating thermal loading presents an obstacle to inexpensive construction of the pressure housing for such sterilization chambers. Otherwise, it cannot be ensured that the instruments will be sterilized as required.

OBJECT AND SUMMARY OF THE INVENTION

Therefore, the primary object of the present invention is to provide a technically simple construction of the pressure housing which satisfies medical requirements, enables automated, dimensionally accurate manufacture, can be used for long periods of operation and further simplifies operation of the sterilization device.

This object is met, according to the invention, in that the walls making up the top, sides and bottom of the pressure housing of the sterilization chamber are individual, detachable, thermally insulating plates which are arranged in central openings of at least two identically constructed frame parts held in positive engagement in a carrier and are held so as to contact the inner edges of the openings in a positive engagement.

According to another feature of the invention, the frame parts of one outer edge have associated hook-shaped continuations which face away from one another, longitudinally graduated or stepped openings of the carrier being associated with these continuations in such a way that the continuations, after being inserted in the respective longer portion of the openings and displaced transversely to the openings (in the y direction), engage under the respective shorter portion of the openings and are held in this position by continuations at the lower wall of the detachable plate forming part of the sterilization chamber, which continuations engage in corresponding openings in the carrier.

In so doing, the maximum width of the openings corresponds to twice the material thickness of the frame parts, the length of the longer portions corresponds to the width of the hook-shaped continuations and the length of the shorter portions of the openings corresponds to the width of the base of the continuations.

According to another feature of the invention, the plates have grooves which enclose the inner edges of the openings of the frame parts in the assembled state so that the walls are held at the carrier in a reliable manner.

To facilitate operation of the sterilization vessel, the upper wall of the pressure housing is provided with a metal holder to receive a cover which is held in a springing manner in its inactive position and has a disk which has an aperture for passage of steam and serves to support a resilient rubber seal forming its edge region and corresponding to the free upper edge of the sterilization vessel to be inserted in the pressure housing.

The deceptively simple idea underlying the invention consists in providing only walls for the sides, top and bottom of the pressure housing as part of the sterilization chamber, constructing these walls as individual plates and arranging these plates in the openings of frame plates so as to be braced against one another at their edge regions. The tolerances which are required in order for the sterilization space formed by the sterilization vessel on the one hand and by the sterilization chamber on the other hand to be tight against pressure are ensured, according to the invention, by plane individual parts which are very easy to manufacture and assemble.

Further, the operating reliability of steam sterilization devices is substantially improved by the pressure housing according to the invention, since the cover is pressed against the upper edges of the sterilization vessel in a pressure-tight manner against the action of the springs holding it in the open position when steam is fed into the pressure housing and is held there until the supply of steam is cut off. Another advantage of the construction according to the invention consists in that the sterilization vessel is automatically released when interrupting the supply of steam for the purpose of removing the sterilized instruments. The sterilization vessel can thus be removed when the sterilization chamber is open, which affords significant convenience of operation for removing and loading medical instruments, implants and the like. Also, walls which may have been damaged can be changed quickly by the user—i.e., without the need for specially trained service personnel.

A substantial reduction in weight is brought about by the construction according to the invention. Another advantage of the invention consists in that by selecting appropriate materials, preferably thermally insulating plastics for the walls of the sterilization chamber and metal for the frame parts, there is no need for additional insulation of the sterilization space relative to the structural component parts enclosing it. In particular, with respect to the selection of material for the walls, it is absolutely necessary that there be no health risk due to contamination of the goods to be sterilized by material components, e.g., mineral fibers, even after prolonged use.

Of course, it must be ensured that the material selected for the walls of the sterilization chamber have the least possible propensity to absorb water, that it be highly resistant to temperature and be dimensionally stable.

Further, recyclable material should be used for the walls if possible.

In the following, the invention is described with reference to an embodiment example shown more or less schematically in the drawing.

BRIEF DESCRIPTION OF THE DRAWINGS

In the drawings:

FIG. 2 is a perspective view of a sterilization vessel for receiving medical instruments and implants which is constructed differently than that shown in FIG. 1 and is to be inserted in a pressure housing of a sterilization chamber, this pressure housing, which is only shown in part, forming the subject matter of the invention;

FIG. 3 is a front view in partial section showing the pressure housing, according to the invention, which forms part of the sterilization chamber;

DESCRIPTION OF THE PREFERRED EMBODIMENTS

Figure 1:
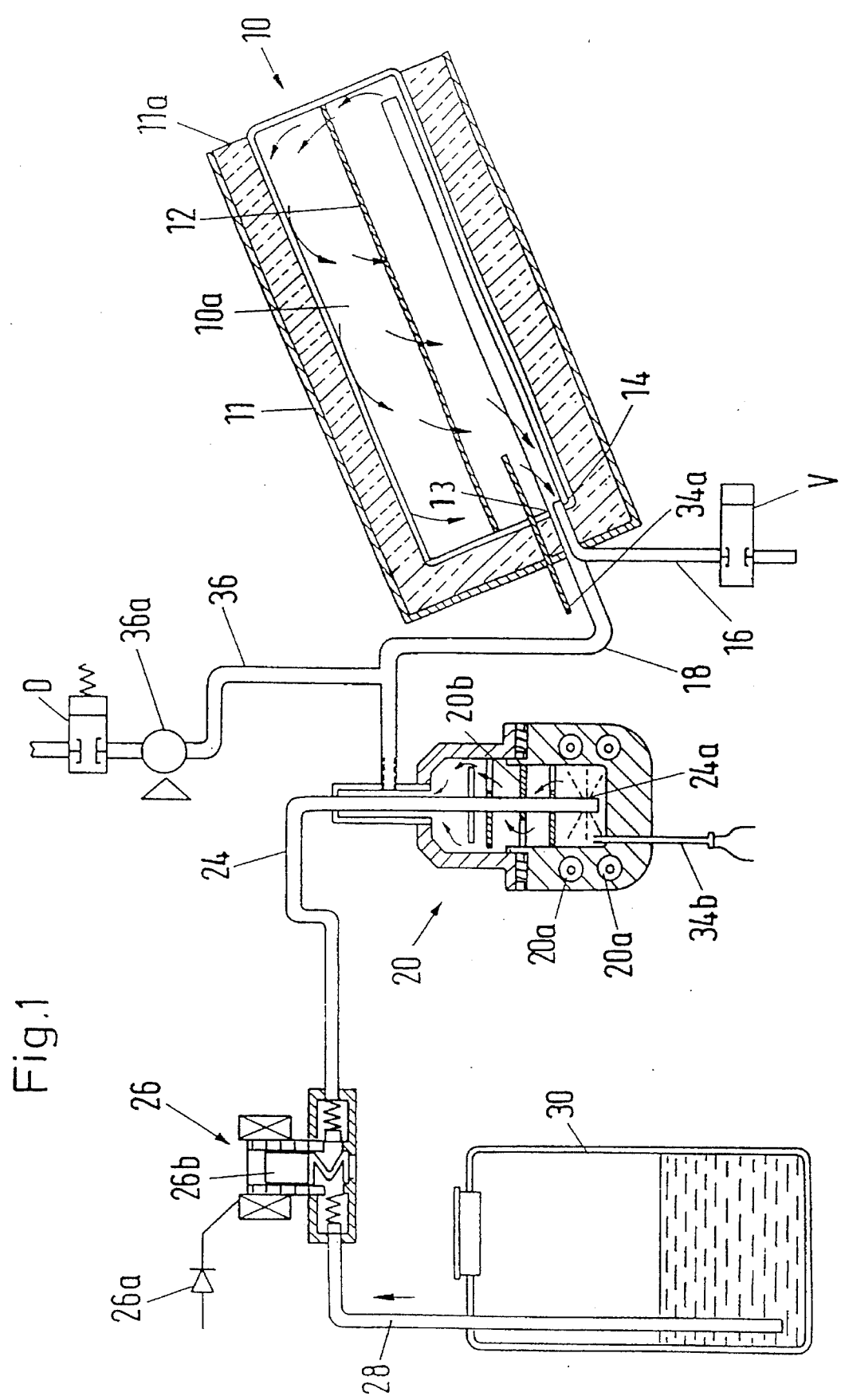
FIG. 1 is a top view of an arrangement for sterilizing medical instruments and implants with a sterilization vessel which is arranged in a holding device.

As will be seen from FIG. 1, a sterilization vessel 10 which is tilted relative to the horizontal line is provided for sterilizing medical instruments and implants by steam. The sterilization vessel 10 can be inserted into a recess of a stationary holding device 11 having thermal insulation 11a. The sterilization vessel has a receptacle plate 12 constructed as a perforated plate for receiving the medical instruments and implants to be sterilized. The holding device 11 has an outlet line 16 for air and condensation projecting through an outlet opening 13 in the sterilization vessel and a steam feed line 18 projecting through an inlet opening 14 into the sterilization vessel, so that both lines project, at a distance from one another, into the space 10a enclosed by the sterilization vessel.

The air and condensation outlet line 16 can be connected to the outside air via a valve V, while the steam feed line 18 is connected with a steam generator 20. The steam chamber of the steam generator 20 is heated by electrical heating elements 20a and is supplied with water in a pulsed manner via a feed line 24 having outlet openings 24a at its end. Direct injection of boiling water into the steam feed line 18 is prevented via splash plates 20b which are arranged in the interior of the steam chamber.

A proportioning pump 26 which communicates, via a suction line 28, with a tank 30 containing distilled water is incorporated in the feed line 24 supplying the steam generator with water. The proportioning pump 26 is driven by means of a piston 26b actuated by an electromagnet which is powered via a diode 26a. The temperatures in the steam chamber of the steam generator and in the sterilization vessel are measured via thermal gauges 34a and 34b.

Finally, the sterilizing chamber can be connected, via a branch line 36 and a pressure regulator 36a, with a compressed-air source (not shown) which can be switched on via a valve D in order to cool and dry the instruments and implants at the end of the sterilizing process.

The sequence of a sterilizing process—in which the blast of steam exiting from the steam feed line passes through the sterilization vessel in a surge—is controlled via a control device, not shown. This process and the associated process for operating the described arrangement are not the subject of the present invention and are shown and described in the aforementioned EP 0 429 960 A2.

The pressure housing, designated in its entirety by 100, which forms part of the sterilization chamber and takes the place of the holding device 11 will now be described with reference to FIGS. 2 to 6.

Figure 4:
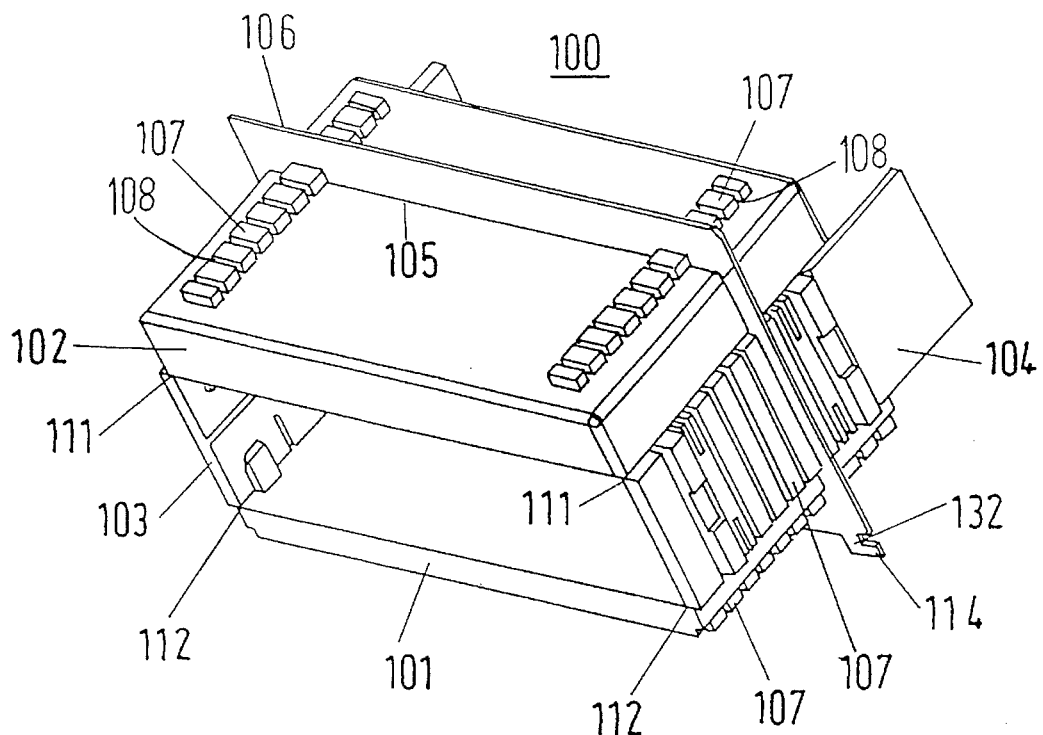
FIG. 4 is a perspective view of the walls of the plates forming the pressure housing according to FIG. 2.
Figure 5:
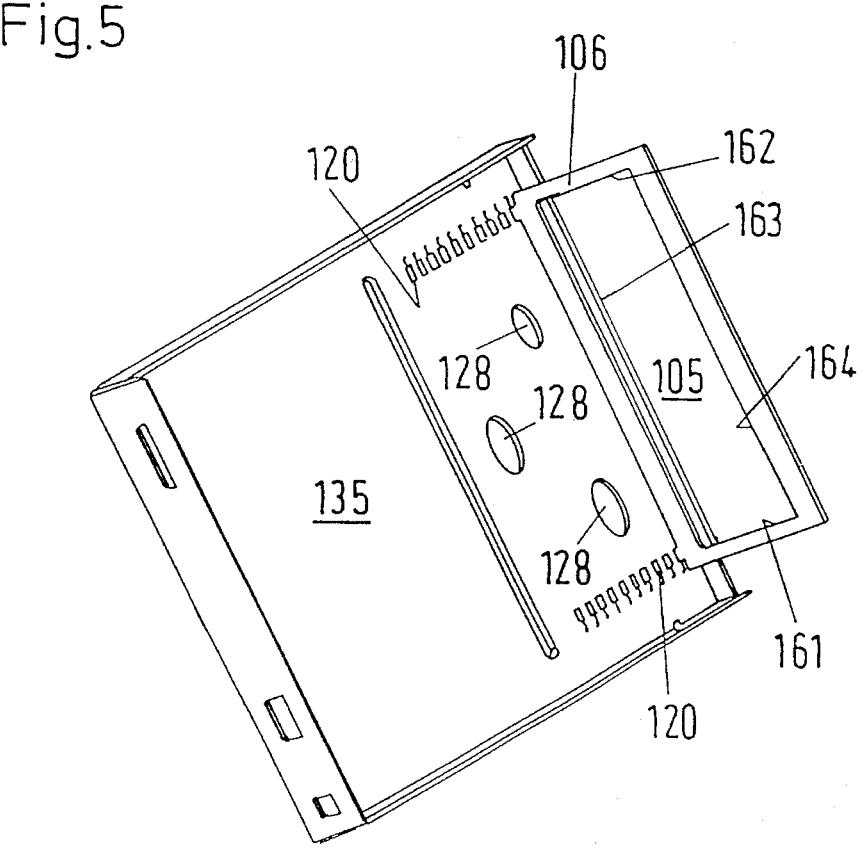
FIG. 5 is a perspective view of the carrier holding the pressure housing according to FIG. 2.

As will be seen in particular from FIG. 4, the pressure housing 100 has four walls which are formed as detachable plates 101, 102, 103 and 104 and are held in contact at the inner edges of centric openings 105 of frame parts 106 as is shown particularly clearly in FIG. 3. This is effected with the assistance of grooves 108 which are formed by projections 107 arranged at the outward facing surfaces of the plates 101–104, the frame parts 106 engaging in these grooves (see FIG. 4). The plates 101 to 104 forming the walls of the pressure housing 100 are embedded in the frame parts 106 in such a way that the abutting edge faces 111/112 of plates 101/102 and 103/104 close with one another so that plates 103 and 104 are spacer plates.

The frame parts 106 have hook-shaped continuations 114 and 115 which are associated with one outer edge at a distance from one another. The pressure housing 100 can be locked by means of these continuations 114, 115 on a carrier 135 via openings 120 which contains a varying width as will be seen particularly from FIGS. 5 and 6.

Figure 6:
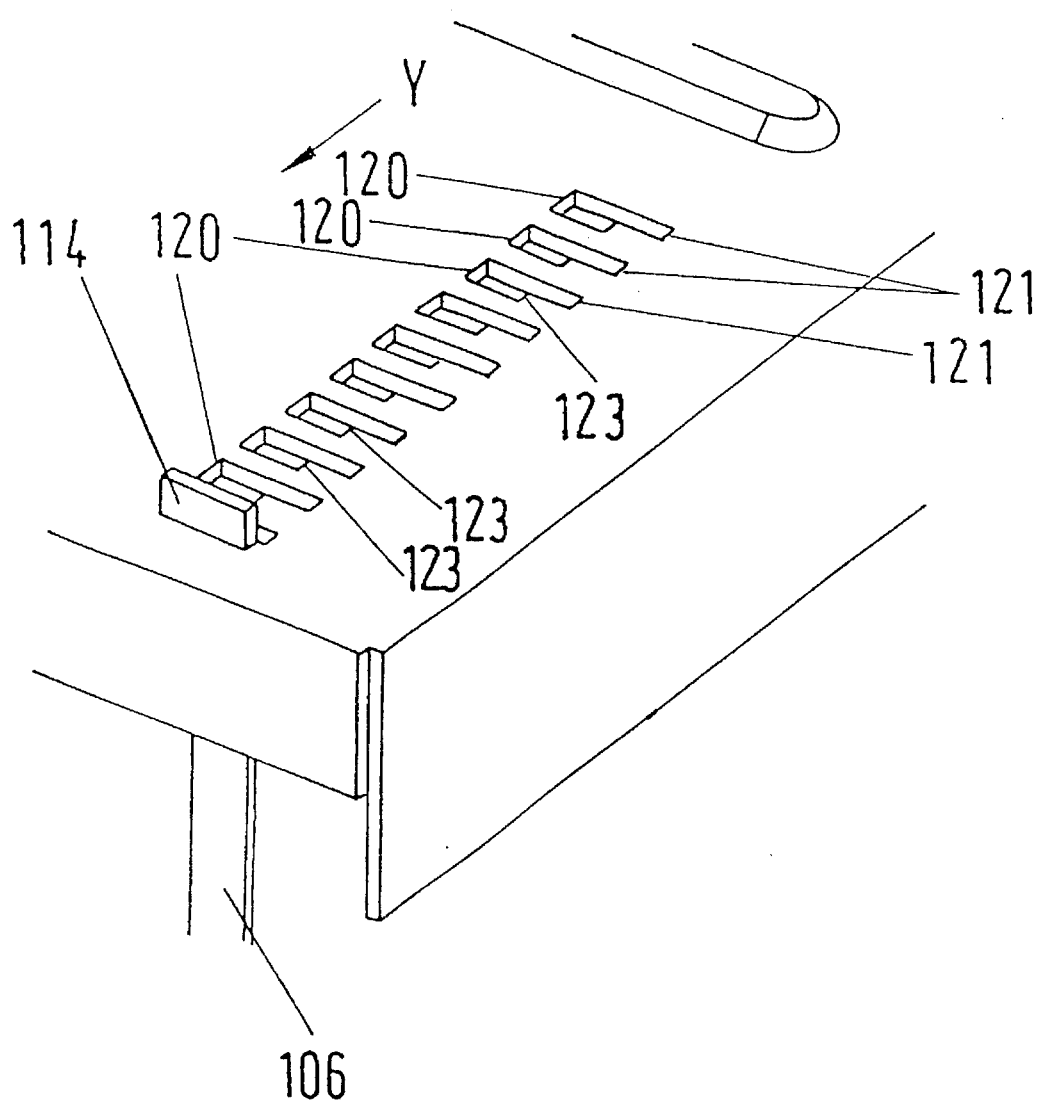
FIG. 6 shows an enlarged detail from FIG. 5.

The graduated openings 120 in the carrier 135 can be seen most clearly in FIG. 6 and, in each instance, have a longer part 121 and a shorter part 123, each of which corresponds in width to the material thickness of the frame part 106. The longer part 121 is adapted in length to the length of the continuations 114, 115 of the frame part 106 and the shorter part 123 is adapted in length to the length of the base 132 of the continuations in such a way that they are locked in the carrier when a frame part is inserted into the openings in the region of the longer part and the frame parts are displaced in the direction of the y axis (see FIG. 6). In this locked position, the frame parts 106 are held at the lower wall 101 by continuations 125 which engage in corresponding openings 128 in the carrier 135 in the position shown in FIG. 3. As will be seen from FIG. 5, the carrier 135 serves as a chassis for the sterilization device, not shown here (see FIG. 1).

As will be seen from FIG. 3, the side of the upper wall 102 facing the sterilization vessel 130 has a cylindrical metal holder 146 for receiving a cover 145 which is held in its inactive position in a springing manner by means of springs 152 and has a disk 138 provided with an aperture 151 for the entry of steam. The disk 138 serves as a support for a resilient rubber seal 143 which forms its edge region and corresponds to the free upper edge 134 of the sterilization vessel 130. As is shown in FIG. 3, this rubber seal is roughly L-shaped in cross section; one of its legs 148, forming the base, encloses the disk 138 of the cover and forms a sealing face for the sterilization vessel, while the other leg 149 forms a guide face contacting the lateral inner surface of the metal holder 146 and has a sealing lip 147. Thus, the metal holder 146 which is cylindrical and the cover 145 corresponding thereto which is piston-shaped both maintain a rectangular cross-section with rounded corners so that they can engage one another in a sealing manner (see FIG. 3).

Since the disk 138 has an aperture 151 for the transfer of hot steam, the surface of the cover 145 facing the sterilization vessel 130 and the surface of the cover 145 facing the upper wall 101 are constructed with different dimensions so that when steam is supplied, the sterilization vessel 130 is held so as to be closed in a pressure-tight manner via the cover by means of the different area pressure which is then effected.

Thus, the cover 145 moves down against the action of the spring under the influence of steam and moves upward under the influence of the spring as soon as the sterilization process is concluded and the steam has escaped so that the sterilization vessel 130 is released.

The frame parts 106 are made from metal and can be produced in series in a simple manner so as to fit accurately with respect to the sterilization chamber associated with the sterilization device, not shown, and with respect to the opening 105. This is equally true of the plates 101 to 104 produced from plastic.

Further, as concerns its assembly in an auxiliary device in technical respects relating to manufacture, the described construction has the advantage that the plates 101 to 104 are inserted into the openings 105 so as to be oriented toward the inner edges 161 to 164 in the following sequence: 101, 102 and 103, 104, and are subsequently pressed against the inner edges of the openings 105 of the frame parts 106 by their grooves formed by the projections 107 so that the grooves enclose the inner edges of the openings 105. After the pressure housing which is formed in this way is inserted into the openings 120 of the carrier 135 and the continuations 125 of the wall 101 are displaced in the y direction and pressed into the openings 128 of the carrier 135, the pressure housing is locked in a positive engagement with the carrier.

In this deceptively simple manner, the described construction enables rapid assembly with the use of standardized structural component parts which are simple to produce and fit exactly.

While the foregoing description and drawings represent the preferred embodiments of the present invention, it will be obvious to those skilled in the art that various changes and modifications may be made therein without departing from the true spirit and scope of the present invention.

What is claimed is:

1. A pressure containment system for receiving a sterilization vessel, said pressure containment system comprising:

a sterilization chamber having top, side and bottom walls, said walls being individual thermally insulating plates with grooves which are formed by projections arranged on outward facing surfaces of the plates;

a carrier; and at least two identically constructed frame parts held in engagement with said carrier, said frame parts having central openings defined therein; wherein, said plates are arranged in said central openings and secured by inner edges of said central openings which engage said grooves;

an outer edge of said frame parts includes hook-shaped projections, said carrier includes (i) a first set of openings to receive said hook-shaped projections, where each of said first set of openings consists of a first width and a second width, said first width being larger than said second width, and a length of said first set of openings is greater than a length of said hook-shaped projections, and (ii) a second set of openings said hook-shaped projections are inserted in said first width of the first set of openings and displaced transversely into said second width of the first set of openings and, said frame parts are held in position by continuations which project from said bottom wall of the sterilization chamber into said second set of openings defined in the carrier.

2. The pressure containment system according to claim 1, wherein said length of said first set of openings corresponds to twice a material thickness of the frame parts, said first width of said first set of openings corresponds to a first width of said hook-shaped continuations and, said second width of said first set of openings corresponds to a second width of said hook-shaped continuations.

3. The pressure containment system according to claim 1, wherein grooves which are formed by projections arranged on outer surfaces of said plates enclose the inner edges of the openings of the frame parts in an assembled state.

4. The pressure containment system according to claim 1, where the top wall of said sterilization chamber includes a metal holder for receiving a cover, wherein said metal holder retains said cover by use of a spring, said cover includes a disk which has an aperture for allowing a passage of steam and said disk supports a resilient rubber seal forming its edge region.

5. The pressure containment system according to claim 4, wherein a surface of the cover facing the sterilization vessel and a surface of the cover facing the metal holder are constructed with different dimensions.

6. The pressure containment system according to claim 4, wherein the metal holder and the cover maintain a rectangular cross-section with rounded corners so that they can engage one another in a sealing manner.

7. The pressure containment system according to claim 6, wherein the plates are made from plastic and the frame parts are made from metal.

* * * * *